United States Patent [19]

Dumoulin

[11] Patent Number: 5,285,261
[45] Date of Patent: * Feb. 8, 1994

[54] DUAL INTERFEROMETER SPECTROSCOPIC IMAGING SYSTEM

[75] Inventor: Charles L. Dumoulin, Ballston Spa, N.Y.

[73] Assignee: General Electric Company, Schenectady, N.Y.

[*] Notice: The portion of the term of this patent subsequent to Oct. 22, 2008 has been disclaimed.

[21] Appl. No.: 909,277

[22] Filed: Jul. 6, 1992

[51] Int. Cl.⁵ .................. G01N 21/00; G01B 11/00
[52] U.S. Cl. .................. 356/432; 356/345; 356/357; 356/358; 356/360
[58] Field of Search ........ 356/432, 345, 355, 357–358, 356/360

[56] References Cited

U.S. PATENT DOCUMENTS

| | | | |
|---|---|---|---|
| 4,044,257 | 8/1977 | Kreuzer | 250/344 |
| 4,581,939 | 4/1986 | Takahashi | 356/432 X |
| 4,710,030 | 12/1987 | Tauc et al. | 356/432 |
| 4,750,822 | 6/1988 | Rosencwaig et al. | 356/445 |
| 4,784,494 | 11/1988 | Pawliszyn | 356/432 |
| 4,808,828 | 2/1989 | Kitamori et al. | 250/458.1 |
| 4,874,251 | 10/1989 | Thomas et al. | 356/432 |
| 5,060,248 | 10/1991 | Dumoulin | 378/53 |
| 5,062,715 | 11/1991 | Nakata et al. | 356/432 |
| 5,136,172 | 8/1992 | Nakata et al. | 356/432 |
| 5,170,217 | 12/1992 | Nishimoto et al. | 356/345 X |

FOREIGN PATENT DOCUMENTS 352789 1/1990 European Pat. Off. .

OTHER PUBLICATIONS

Glen M. Robinson, Ph.D, David M. Perry, and Richard W. Peterson, "Optical Interferometry", Scientific American Jul. 1991, pp. 445–449.

Primary Examiner—Robert J. Warden
Assistant Examiner—Krisanne M. Thornton
Attorney, Agent, or Firm—Lawrence P. Zale; Marvin Snyder

[57] ABSTRACT

To obtain spectra from the surface of a sample, a first of a pair of interferometers includes a broadband radiation source and modulates the radiation at a frequency which is inversely proportional to wavelength. The modulated radiation impinges on the surface of interest where it is absorbed. The absorption of radiation causes the surface of the sample to expand. This change in dimension is then detected by a second interferometer which employs a monochromatic radiation source to measure the instantaneous distance between the sample surface and the second interferometer. The detection system of the second interferometer can be an imaging device such as a video camera to obtain the spatial distribution of chemical composition of the sample surface.

12 Claims, 4 Drawing Sheets

DUAL INTERFEROMETER SPECTROSCOPIC IMAGING SYSTEM

CROSS REFERENCE TO RELATED APPLICATIONS

This application is related to applications "SPECTROSCOPIC IMAGING SYSTEM USING A PULSED ELECTROMAGNETIC RADIATION SOURCE AND AN INTERFEROMETER", Ser. No. (07/909,276 filed Jul. 6, 1992), and "SPECTROSCOPIC IMAGING SYSTEM WITH ULTRASONIC DETECTION OF THE ABSORPTION OF MODULATED ELECTROMAGNETIC RADIATION" Ser. No. (07/909,275 filed Jul. 6, 1992) both by Charles L. Dumoulin, both filed simultaneously with this application, and both assigned to the present assignee.

BACKGROUND OF THE INVENTION

1. Field of the Invention

The present invention relates to optical spectroscopy and more particularly to the optical spectroscopy of a surface of a sample.

2. Description of Related Art

Absorption and transmission spectra of a sample can be obtained using electromagnetic radiation for the purpose of identifying chemical types. Certain spectral regions are of greater use than others. The spectral regions of greatest use are those in which chemical species contained within the sample, absorb radiation at characteristic wavelengths. The absorbed radiation can be detected directly, re-emitted by the sample or cause the sample to fluoresce. Spectroscopic measurements of absorption, emission and fluorescence using infra-red, visible and ultra-violet light are widely used for sample analysis. Unfortunately, many of these techniques are not well suited to applications where the sample has rough surfaces. Radiation is scattered by rough surfaces thereby making measurement of reflection difficult. Techniques requiring transmission through a sample, are difficult or impossible using opaque samples.

One technique which has proved useful for the spectroscopic analysis of rough surfaces is Photo-Acoustic Spectroscopy. With this technique, a monochromatic light source is chopped to create a pulsed light source. The pulsed light is directed to impinge on the surface of the sample. The pulsed light is at a wavelength which is absorbed by the sample, causing a periodic heating of the surface which in turn causes the surface to expand and contract. This movement generates sound waves which propagate through the gas above the surface and are detected by a sensitive microphone. Spectra of the surface are generated by varying the wavelength of the incident radiation. Unfortunately, the detection efficiency of Photo-Acoustic procedures is low with respect to other optical analysis methods, and thus the technique is not easily applied to small samples.

A non-spectroscopic technique which has been demonstrated to be useful for the analysis of surface roughness is Optical Interferometry. In this technique, monochromatic light impinges upon a sample surface resulting in interferograms. The resulting interferograms are then used to generate digital maps of the surface. While this technique detects the physical features of a surface, it is not capable of providing information about the surface's chemical composition. A review of the techniques of optical interferometry of surfaces is described in *Optical Interferometry* Scientific American July 1991, pages 44–49 by Glen M. Robinson, Ph.D., David M. Perry, and Richard W. Peterson which is hereby incorporated by reference.

Presently there is a need for an analytical system capable of detecting the optical spectra of selected chemical types for samples having rough surfaces, with high sensitivity.

SUMMARY OF THE INVENTION

A spectroscopic imaging system according to the invention includes a first interferometer employing a broadband electromagnetic radiation source. A movable mirror of the first interferometer when moved linearly, causes the amplitude of each one of different wavelengths of the broadband radiation source to be modulated at a frequency which is inversely proportional to its respective wavelength. The modulated light impinges on the surface of the sample of interest, where it is absorbed, causing the temperature of the surface to rise and the surface to expand. Since the radiation is modulated (i.e. the amplitude of a selected wavelength varies sinusoidally with time) heating of the surface is periodic. This results in a periodic expansion and contraction of the surface at a rate which is inversely proportional to the wavelength of the absorbed radiation.

A second interferometer reflects monochromatic electromagnetic radiation off of the sample surface. Unlike the radiation source used to modulate the surface dimension, the wavelength of continuous radiation source is chosen to minimize absorption of the radiation by the sample surface. The reflected monochromatic radiation is sensed by the second interferometer to measure the instantaneous distance between the sample surface and the second interferometer. This distance varies with time at a frequency inversely proportional to the wavelength of absorbed radiation. The amplitude of the distance changes is proportional to the degree of absorption of the broadband radiation source. Therefore, the changes in distance measured by the second interferometer indicates the absorption properties of the sample surface.

In a second embodiment of the invention, an imaging device capable of detecting optical intensity at a plurality of spatial locations, such as a video camera, is used as the detection device. At least three images are obtained, each at a different distance between the surface and the second interferometer. Each image is a different interferogram of the surface which may be combined to form a map of the surface.

OBJECTS OF THE INVENTION

It is an object of the invention to provide a system for obtaining absorption spectra from a rough surface of a sample.

It is another object of the invention to provide a system for obtaining distribution images of surfaces chemical types which absorb radiation at selected wavelengths.

It is another object of the invention to provide a system for obtaining absorption spectra from a non-transparent sample.

BRIEF DESCRIPTION OF THE DRAWINGS

The features of the invention believed to be novel are set forth with particularity in the appended claims. The invention itself, however, both as to organization and method of operation, together with further objects and advantages thereof, may best be understood by reference to the following description taken in conjunction with the accompanying drawing in which:

DETAILED DESCRIPTION OF THE INVENTION

Figure 1:
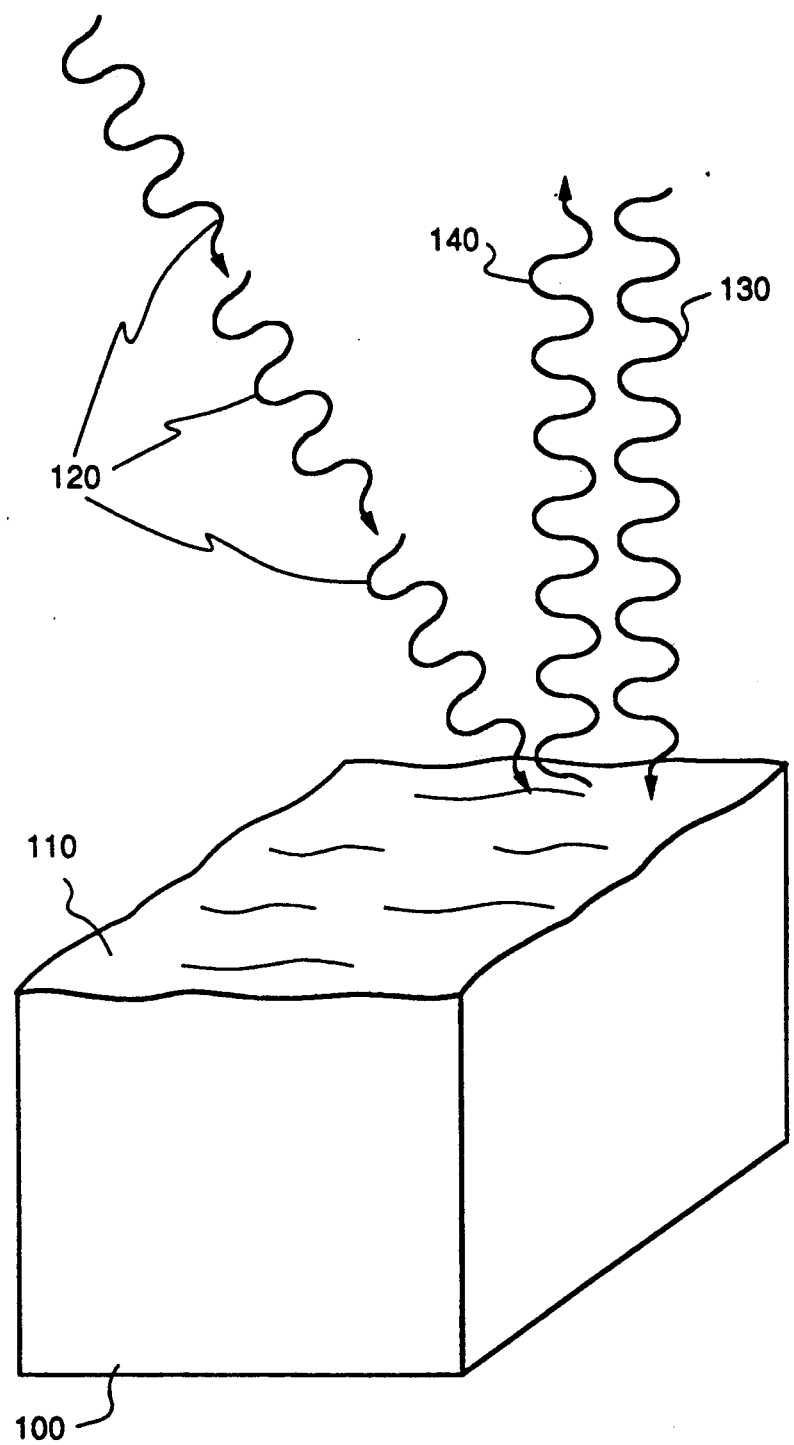
FIG. 1 is a perspective view of a sample surface absorbing radiation from one source and reflecting radiation from a second source.

FIG. 1 shows a sample 100 having a surface 110 to be analyzed. A sample excitation beam 120 of electromagnetic radiation from a first interferometer means using a broadband source impinges upon surface 110. This radiation has spectral components which are modulated at a frequency which is inversely proportional to wavelength. An amount of sample excitation beam 120 is absorbed by surface 110 which is characteristic of specific chemical components.

A measurement beam 130 of monochromatic electromagnetic radiation from a second interferometer means impinges on surface 110 and is reflected to produce a return beam 140 of electromagnetic radiation. The wavelength of the monochromatic source for measurement beam 130 is chosen to minimize absorption of this radiation by sample 100. Return beam 140 is scattered by the rough surface, but a sufficient amount of radiation is reflected back to the second interferometer means where it is used to make an accurate measurement of the displacement of surface 110 with respect to the second interferometer means.

Figure 2:
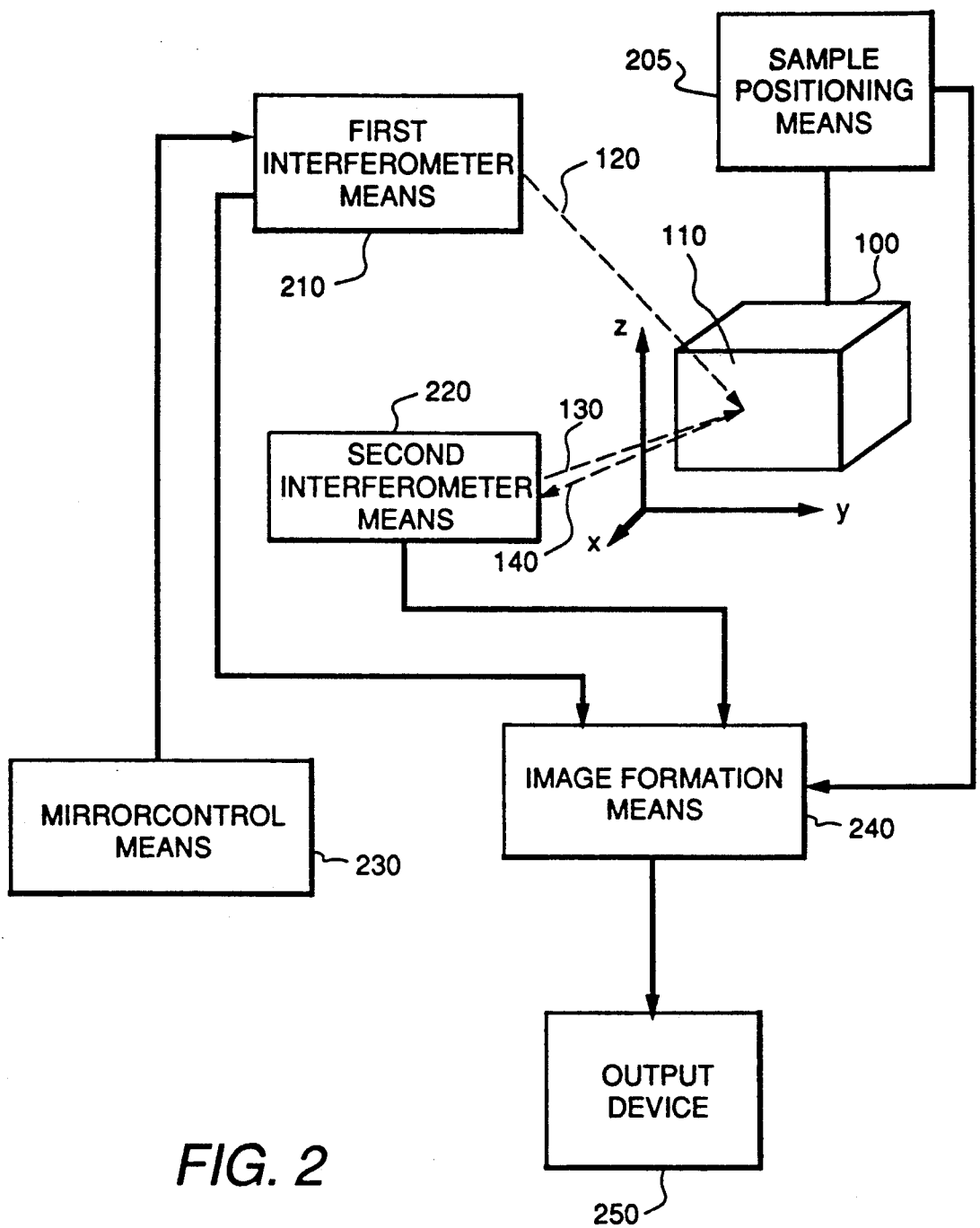
FIG. 2 is a block diagram of one embodiment of the present invention in which two interferometer means are used to obtain spectra from a selected sample surface.

FIG. 2 is a schematic diagram of one embodiment of the present invention. Here, sample 100 is positioned at a desired location in three dimensions (x,y,z) relative to the system by a sample positioning means 205. Surface 110 of sample 100 is then irradiated with radiation from first interferometer 210 and second interferometer 220. A mirror control means 230 is used to control the motion of mirrors within first interferometer means 210. Signals indicating the motion of the mirrors in first interferometer means 210 are sent to an image formation means 240. Signals from second interferometer means 220 are propagated to image formation means 240 substantially simultaneously with the mirror motion information. Signals indicating the position of sample 100 are sent from sample positioning means 205 to image formation means 240. The image formation means 240 employs the signals provided by the first interferometer means 210, second interferometer means 220, and sample position means 205 to generate absorption spectra for a plurality of irradiated points on sample surface 110. An output device 250 manipulates selected portions of the spectra to create maps of chemical types on surface 110. Output device 250 may also execute a number of analytical tests based upon the spatial and spectral information.

Figure 3:
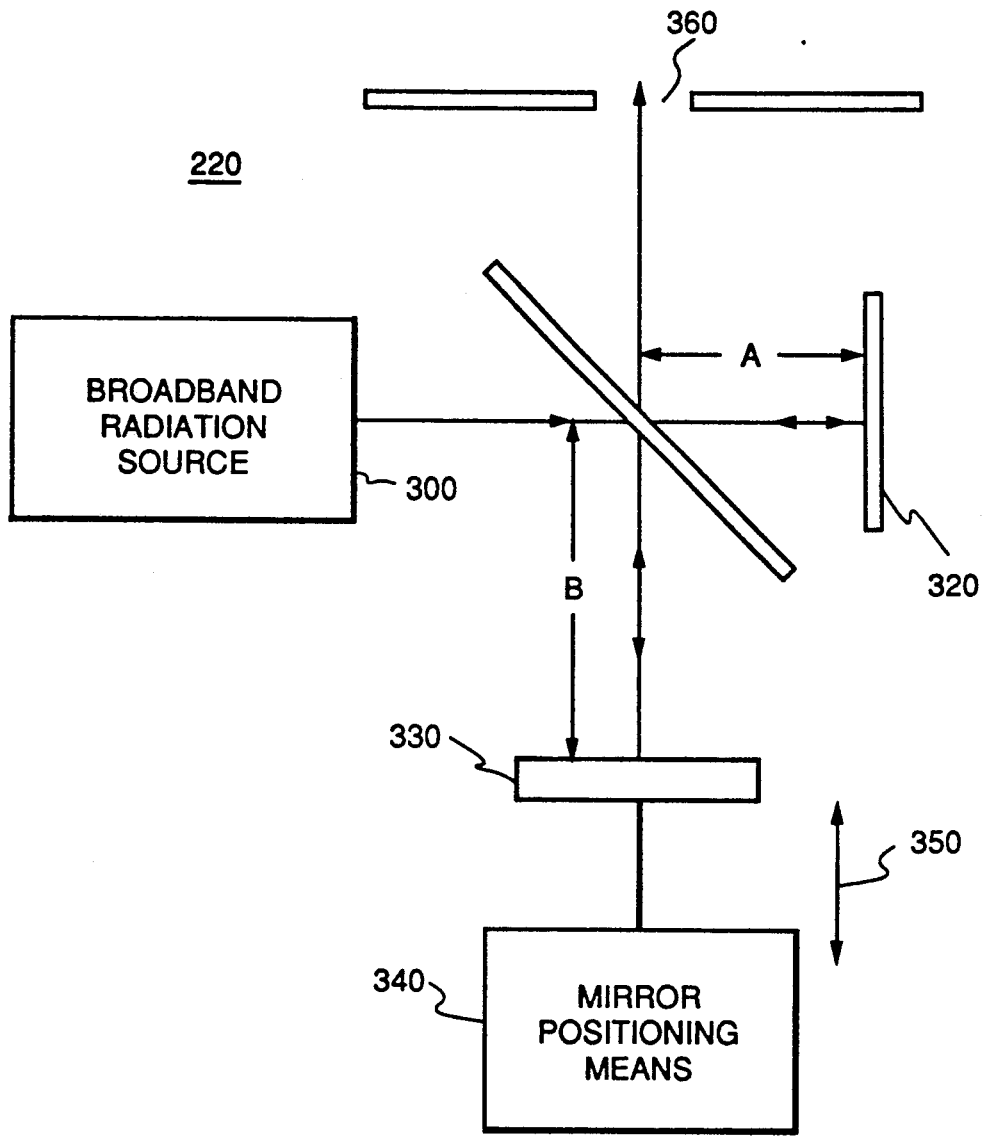
FIG. 3 is a block diagram of one embodiment of the first interferometer means of FIG. 2 used to generate radiation directed at the surface of the sample.

FIG. 3 is a detailed schematic illustration of first interferometer 210 having a broadband radiation source 300 which passes radiation to a beam splitter means 310, such as a half-silvered mirror. The beam splitter means 310 splits radiation from source 300 into a first transmitted beam and a first reflected beam. The first transmitted beam reflects off of a fixed mirror 320 located at a distance A from beam splitter means 310 back to beam splitter 310. Beam splitter 310 creates a second transmitted beam and a second reflected beam from the reflection of the first transmitted beam. The first reflected beam is reflected, at a distance B from the beam splitter, from a movable mirror 330 that is in motion. The first reflected beam impinges upon beam splitter 310 to form a third reflected beam and a third transmitted beam. A mirror positioning means 340, controlled by mirror control means 230 of FIG. 2, causes constant motion of movable mirror 330. When the path lengths A and B of the radiation reflected from the fixed and movable mirrors are equal, the second reflected and third transmitted beams are in phase as they pass through an exit port 360 of the interferometer. As the mirror position is varied along its movement axis 350, the path lengths A & B are no longer equal and the two beams have a phase relationship determined by the difference in path lengths and the wavelengths of the radiation; that is, they constructively and destructively interfere with each other, causing modulation of amplitude for each wavelength. For example, if movable mirror 330 is positioned such that the difference in path lengths is an integral number of wavelengths, the two beams, for a given wavelength, will be in phase as they exit the interferometer, and will combine constructively. If, on the other hand, the path lengths differ by ½ the wavelength of the radiation, the two beams will be 180° out of phase, for a given wavelength, as they exit the interferometer, and they will combine destructively so that no net radiation at that frequency will exit the interferometer.

Broadband source 300 in the first interferometer generates radiation having a distribution of wavelengths. If the path lengths A and B are equal, all wavelengths of the radiation from the broadband source will be propagated through the interferometer. As the movable mirror changes position, radiation at each wavelength will go in and out of phase. If the mirror movement is constant with time, the radiation exiting the interferometer will be modulated at a frequency which is inversely proportional to the wavelength of the radiation.

Figure 4:
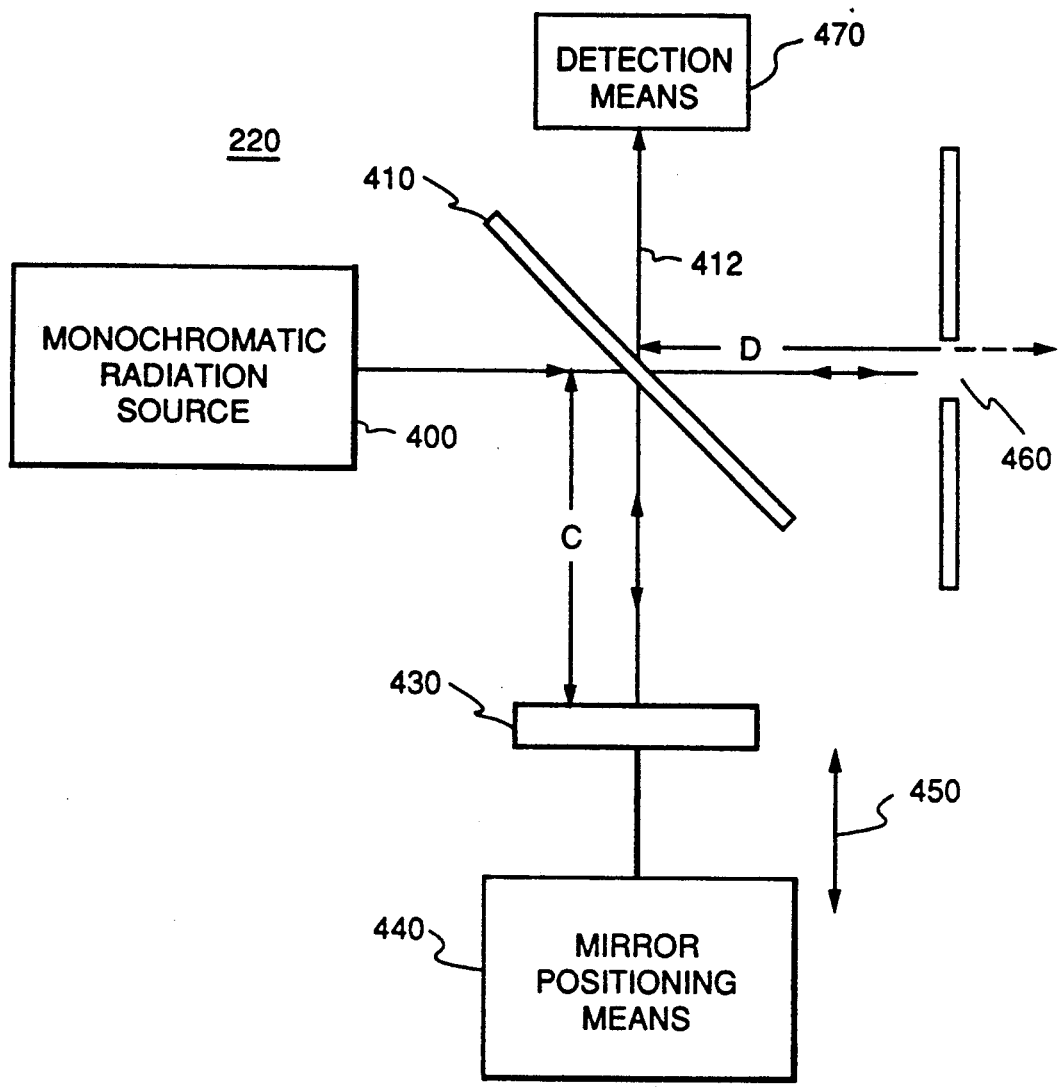
FIG. 4 is a block diagram of one embodiment of the second interferometer means of FIG. 2 used to measure surface displacement caused by the absorption of radiation from the first interferometer.

The broadband radiation from the first interferometer impinges upon the surface 110 of sample 100 of FIG. 1 where some fraction of it is absorbed. The absorption of radiation causes the temperature of the immediate area of the surface to rise. This rise in temperature in turn causes the material in the surface to expand. Since the radiation is modulated (i.e. the amplitude of a selected wavelength varies sinusoidally with time) heating of the surface is periodic. This results in a periodic expansion and contraction of the surface at a rate which is inversely proportional to the wavelength of the absorbed radiation. This expansion and contraction is accurately measured with the second interferometer shown in greater detail in FIG. 4.

In second interferometer means 220 (shown in FIG. 2), a monochromatic radiation source 400 propagates radiation of a small band of wavelengths to a beam splitter means 410. The radiation is split into a first partially transmitted beam and a first partially reflected beam. The first reflected beam reflects off a movable mirror 430 back to beam splitter 410 creating a second partially reflected beam and a second partially transmitted beam. In this embodiment, movable mirror 430 remains fixed, but can be adjusted by a mirror positioning means 440 by moving it along a selected axis 450 if desired. The first partially transmitted beam propagates through an exit port 460 of the second interferometer where it impinges on the surface of the sample and a portion is reflected back to beam splitter 410 creating a third partially reflected beam and a third partially transmitted beam. The third partially reflected beam is combined with the second partially transmitted beam to create a detection beam 412. If the distance C, between the beam splitter and mirror 430, and distance D, between the beam splitter and the sample surface, differ by an integral number of wavelengths of the monochromatic radiation source, radiation detected at the detection means 470 is in phase and combines constructively. If, on the other hand, the distances C and D are not integral multiples of the wavelength, some destructive interference will occur. As the surface of the sample expands and contracts with time responsive to the radiation from the first interferometer, the distances C and D will change with respect to each other. Consequently, the monochromatic radiation impinging on detection means 470 will be modulated at a frequency inversely proportional to the wavelength of the radiation absorbed by sample 100 and at an amplitude commensurate with the degree of absorption.

A Fourier transform is performed by image formation means 240 of FIG. 2 on the measured changes in distance acquired over time d(t) to arrive at D(f) a spectrum of absorption amplitude vs. frequency of absorption for each selected point of the surface sample.

If detection means 470 of the second interferometer does not resolve spatial information, the second interferometer detects distances from a region of the surface which is limited by the focal spot size of the second interferometer. If, on the other hand, the detection means employs an imaging device such as a video camera, measurements made at multiple displacements of mirror 430 in the second interferometer along mirror movement axis 450, or conversely movement of sample 100 with respect to the second interferometer, can be used to generate images of surface 110 as described in the aforementioned Robinson et al. paper at pages 44–49.

While several presently preferred embodiments of the novel spectroscopic imaging system have been described in detail herein, many modifications and variations will now become apparent to those skilled in the art. It is, therefore, to be understood that the appended claims are intended to cover all such modifications and variations as fall within the true spirit of the invention.

What is claimed is:

1. A system for creating images representing chemical composition of a sample surface based upon the electromagnetic absorption spectra thereof comprising:
    a) a first interferometer means for irradiating a portion of a sample surface with a time modulated sample excitation beam having a plurality of frequencies, each frequency having an amplitude varying with time inversely according to its frequency;
    b) a second interferometer means for detecting changes in distance over time between said sample surface and the second interferometer responsive to absorption by the sample of the broadband radiation beam generated by the first interferometer; and
    c) image formation means for calculation of absorption spectra of the portion of said sample surface from the detected changes in distance versus time between said sample surface and the second interferometer, for creating absorption spectra for portions of said sample surface from the detected changes in distance indicating chemical composition of said sample surface, and creating an image indicating chemical composition over the portions of said sample surface. ·

2. The system of claim 1 further comprising positioning means for moving said sample relative to the first and second interferometers.

3. The system of claim 1, wherein the first interferometer means comprises:
    a1) a beam splitter for creating a partially transmitted and partially reflected beam from an incident beam;
    a2) a broadband radiation source for creating a broadband radiation beam incident upon the beam splitter such that the beam splitter creates a first transmitted beam and a first reflected beam;
    a3) a fixed mirror for reflecting the first transmitted beam back toward the beam splitter, so as to be split by the beam splitter into a second transmitted and a second reflected beam; and
    a4) a movable mirror being movable in a substantially uniform manner, for reflecting the first reflected beam back to the beam splitter so as to be split into a third transmitted beam and a third reflected beam such that the third transmitted beam constructively and destructively interferes with the second reflected beam to create a time modulated sample excitation beam having a plurality of frequencies, each frequency having an amplitude varying with time inversely according to its frequency.

4. The system of claim 1, wherein the second interferometer means comprises:
    b1) a beam splitter for creating a partially transmitted and partially reflected beam from an incident beam;
    b2) a monochromatic radiation source for creating a radiation beam having a frequency which is reflected from said sample surface, the radiation beam being incident upon the beam splitter causing the beam splitter to create a first transmitted beam and a first reflected beam, the first transmitted beam being reflected off of said source surface back toward the beam splitter which is split by the beam splitter into a second transmitted and a second reflected beam;
    b3) a movable mirror, the movable mirror reflecting the first reflected beam back to the beam splitter which is split into a third transmitted beam and a third reflected beam such that the third transmitted beam constructively and destructively interferes with the second reflected beam creating a detection beam; and
    b4) a detection means for sensing the detection beam and determining changes in distance versus time between the second interferometer means and said sample surface.

5. The system of claim 3 further comprising mirror control means for controlling motion of the movable mirror of the first interferometer and providing information regarding the motion of the movable mirror to the image formation means.

6. The system of claim 4, wherein said detection means simultaneously determines changes in distance between the interferometer means and a plurality of points on said sample surface versus time from the detection beam, thereby obtaining spatially resolved information from the irradiated portion of said sample surface.

7. The system of claim 6 including means for generating images of said sample surface from the detected changes in distances versus time obtained by said detection means in response to broadband sample excitation beam generated by the first interferometer means.

8. The system of claim 3, wherein the broadband radiation source comprises means for generating radiation at a wavelength in one of the group of wavelengths consisting of: infra-red wavelengths, visible light wavelengths and ultra-violet wavelengths.

9. The system of claim 4, wherein the monochromatic radiation source of the second interferometer is a laser.

10. The system of claim 1, wherein the image formation means includes Fourier transformation means for calculating Fourier transform values of the detected changes in distance versus time for at least one point of the irradiated portion of said sample surface to generate an absorption spectrum for the at least one point.

11. The system of claim 10 further including an output device for creating an image indicating distribution of a desired chemical type from the absorption spectrum of sample at the at least one point.

12. A method of creating images representing chemical composition of a sample surface based upon the electromagnetic absorption spectra thereof, comprising the steps of:

a) irradiating a portion of said sample surface with a time modulated output beam having a plurality of frequencies, each frequency having an amplitude frequency of the output beam which varies with time inversely according to its frequency, causing the sample surface to absorb a portion of the output beam and expand periodically changing distance between the sample surface and a measurement point;

b) detecting changes in distance between the sample surface and the measurement point over time using an interferometer;

c) calculating Fourier transform values of the detected changes in distance versus time for at least one point of the irradiated portion of said sample surface; and d) generating an absorption spectrum of said sample surface from the Fourier transform values, indicating chemical composition of said sample surface.

* * * * *